United States Patent [19]

Fox

[11] Patent Number: 5,405,388
[45] Date of Patent: Apr. 11, 1995

[54] BONE BIOPSY IMPLANT

[76] Inventor: William C. Fox, HC2 Box 7050, Pipe Creek, Tex. 78063

[21] Appl. No.: 16,908

[22] Filed: Feb. 12, 1993

[51] Int. Cl.⁶ .............................................. A61E 2/28
[52] U.S. Cl. ..................................................... 623/16
[58] Field of Search ............... 623/16, 18, 66; 606/62, 606/63

[56] References Cited

U.S. PATENT DOCUMENTS

4,880,006  11/1989  Albrektsson et al. ................. 623/66
4,936,851  6/1990  Fox, Jr. et al. ......................... 623/16

Primary Examiner—David Isabella
Assistant Examiner—Debra S. Brittingham

[57] ABSTRACT

A bone biopsy implant having a short cylindrical collar (15) with a removable tapered inner sleeve (40) which together act to facilitate bone sample collection and endoscopic access to the medullary compartment of bone. The collar (15) is provided with a biocompatible outer surface that secures with flutes (17) to resist rotation and circumferential beads (16) to resist pull-out forces. The collar walls on the fluted end strains towards the centerline to facilitate insertion or removal in a hole. The collar (15) is further provided with a flange on one face that has a ramp (18) shaped surface on its end that act together with a similar ramp (20) on the tapered sleeve (40) to cause longitudinal translation of the sleeve when rotated. This sleeve is comprised of three components consisting of a short cylindrical cap (11) that is contoured on the end and has flat regions on the surface suitable for use with a socket wrench, a fluted cylindrical basket (12) that cuts and contains the bone and marrow sample and a cylindrical end-cap (13) having a plurality of threads. The implant includes provision for its insertion and explantation, repeated sampling of bone tissue and fixation and introduction of endoscopic instrument in bone.

13 Claims, 7 Drawing Sheets

BONE BIOPSY IMPLANT

FIELD OF THE INVENTION

The invention described relates broadly to the devices capable of acquiring a physical sample, generally to the field of medical devices and specifically to the acquisition of bone, marrow and cartilage biopsies.

BACKGROUND—RELATED APPLICATIONS

In the prior art, I described in my patent of the analytic bone implant (hereinafter sometimes call the "ABI"), U.S. Pat. No. 4,936,851 issued Jun. 26, 1990 to Fox et al., a device that allows cancellous bone and marrow as well as organs surrounded by hardened cortical bone to be accessed repeatable from the same site with minimal surgical trauma and morbidity. The purpose of gaining repeated access was to provide a means for obtaining a significant sample of cancellous tissue for histologic and morphometric analysis.

A subsequent invention of mine, the cancellous access port (hereinafter sometimes called the "CAP") bone implants are patent pending (Ser. No. 07/575,001, filed Aug. 29, 1990 by Fox et al.). Like the ABI, the CAP can be used for repeated biopsies of osseous tissue. The CAP is novel when configured with a three electrode transducer for electrochemical characterization of biology/biomaterial interfacial reactions.

Through repeated use of the prior art, failures of the mechanism, difficulty in surgical placement and the inability to acquire a biopsy have been encountered, thus a new invention, the bone biopsy implant, was conceived to remedy these failings.

BACKGROUND—PRIOR ART

In the prior art, bone implants have been used to solve health care problems of orthopedic and maxillofacial reconstruction, prosthesis and denture fixation, and fracture stabilization. Additionally, bone implants have been developed to advance the knowledge of bone healing and remodeling as well as the interaction of bone and implant material or devices.

Prior art unrelated to this application which specifically relate to the invention include an optical titanium chamber disclosed by Albrektsson in 1979, a bone ingrowth chamber (hereinafter sometimes called the "BIC") (Albrektsson et al., U.S. Pat. No. 4,880,006, Nov. 14, 1989), and a bone harvest chamber (hereinafter sometimes called the "BHC") (Kalebo in 1987) all of which were developed at the University of Goteborg, Sweden. Together the related and unrelated prior art provide a means for obtaining permanent atraumatic access to otherwise inaccessible biological tissues which are protected or covered by hardened bone structures. However, their capability to obtain a biopsy of cortical bone or cancellous tissue following complete healing and mineralization of this tissue is severely compromised by their design. Finally, unlike the BIC, ABI and CAP which were not designed for long-term use in humans, the BBI is of appropriate size, geometry and contoured to eliminate overlying soft-tissue irritation. The novel claims of this new bone implant are its features that allow reliable biopsy of fully mineralized bone, cartilage and marrow from humans. These novel improvements over the prior art offer significant advantages in implant reliability and performance while decreasing manufacturing cost.

SUMMARY OF THE INVENTION—OBJECTS AND ADVANTAGES

The subject invention relates to a hard tissue implant, referred to herein as a bone biopsy implant (hereinafter sometimes called the "BBI") which can be used in bone or cartilage to biopsy completely healed and mineralized bone tissue and marrow for the assessment of bone marrow cancer and osteoporosis.

The objects and advantages of the preferred embodiment of the BBI are: (11) a collar that does not require a threaded osseous defect, (12) a contoured cap to minimize overlying soft-tissue irritation, (13) a socket-head shaped cap for conventional instruments, (14) a ramp on the mating faces of the collar and cap (or tissue basket) that act to withdraw from bone the rotated cap and biopsy assembly, (15) an externally and internally tapered cutting basket to facilitate withdrawal of the cutting basket from bone and the removal of the biopsy from the lumen of the cutting basket, (16) a plurality of bone ingrowth slots in the cutting basket which can be varied in alignment, number, and placement so that the slot's cutting edge has three directions of cutting action (shear, cut and pull), (17) an elastomeric seal to stop hemorrhage through the implant lumen, (18) a collar with a plurality of flutes cut through the periphery and parallel to the longitudinal axis to resist collar rotation and allow the section of the collar body designed to contact cortical bone to act elastically when pressed into or pulled from a bone defect, (20) a collar that is externally grooved or beaded circumferentially to resist forces tending to pull or push out the implant, and (21) a tissue basket with two capped ends so as to increase cutting basket strength and allow extraction of the biopsy in the direction of the expanding lumen's taper.

The novel three cutting directions and the outside diameter taper of the tissue basket significantly improve the performance of this implant for acquiring tissue and gaining access to bone over the prior art. Additionally, the cutting basket design does not require, as in the case of the ABI, a surrounding cylinder with matching ingrowth slots to create a shearing action between the inner and outer cylinder. Use of the CAP and ABI have shown that the surrounding bone acts like the outer cylinder of the ABI by resisting the shearing action of the basket's cutting edge. The BBI is fabricated from biocompatible materials not limited to titanium and stainless steel.

The embodiment is intended to describe an example and is not intended to limit this invention to just those objects and advantages described.

LIST OF REFERENCE NUMERALS 11. the upper component hexagonal cap of the biopsy assembly
12. the internally and externally tapered middle component cutting basket of the biopsy assembly
13. the lower component end-cap of the cutting basket
14. the off longitudinal axis flutes with sharpened inner edge in cutting basket
15. the collar with withdraw ramp, fluted body, anchor bead and elastomeric seal ring slot
16. collar anchor bead
17. collar flutes
18. collar withdraw ramp
19. elastomeric seal ring in collar lumen
20. biopsy assembly withdraw ramp
21. cortical bone
22. marrow and bone cells
23. cancellous bone trabeculae
24. sharpened cutting edge of a cutting basket flute
25. direction of withdraw due to biopsy assembly rotation and the interaction of the collar and cutting basket ramp
26. direction of rotation of the biopsy assembly when acquiring a biopsy
27. Cartesian coordinate system illustrating the cutting edge direction of movement
28. nut for material fixation mandrel
29. material fixation mandrel
30. mandrel material fixation slot
31. tool driver slot in nut
32. plurality of threads on hexagonal cap
33. tapered lumen of the cutting basket
34. plurality of threads on inner surface of the cutting basket
35. plurality of threads on outer surface of the end-cap
36. tool slot in end-cap
37. recess located in the end face of the collar
38. tapered outer surface of the cutting basket
39. embodiment of the hexagonal cap with hole to receive fixation mandrel and nut
40. biopsy assembly

DESCRIPTION OF THE PREFERRED EMBODIMENTS

Figure 1:
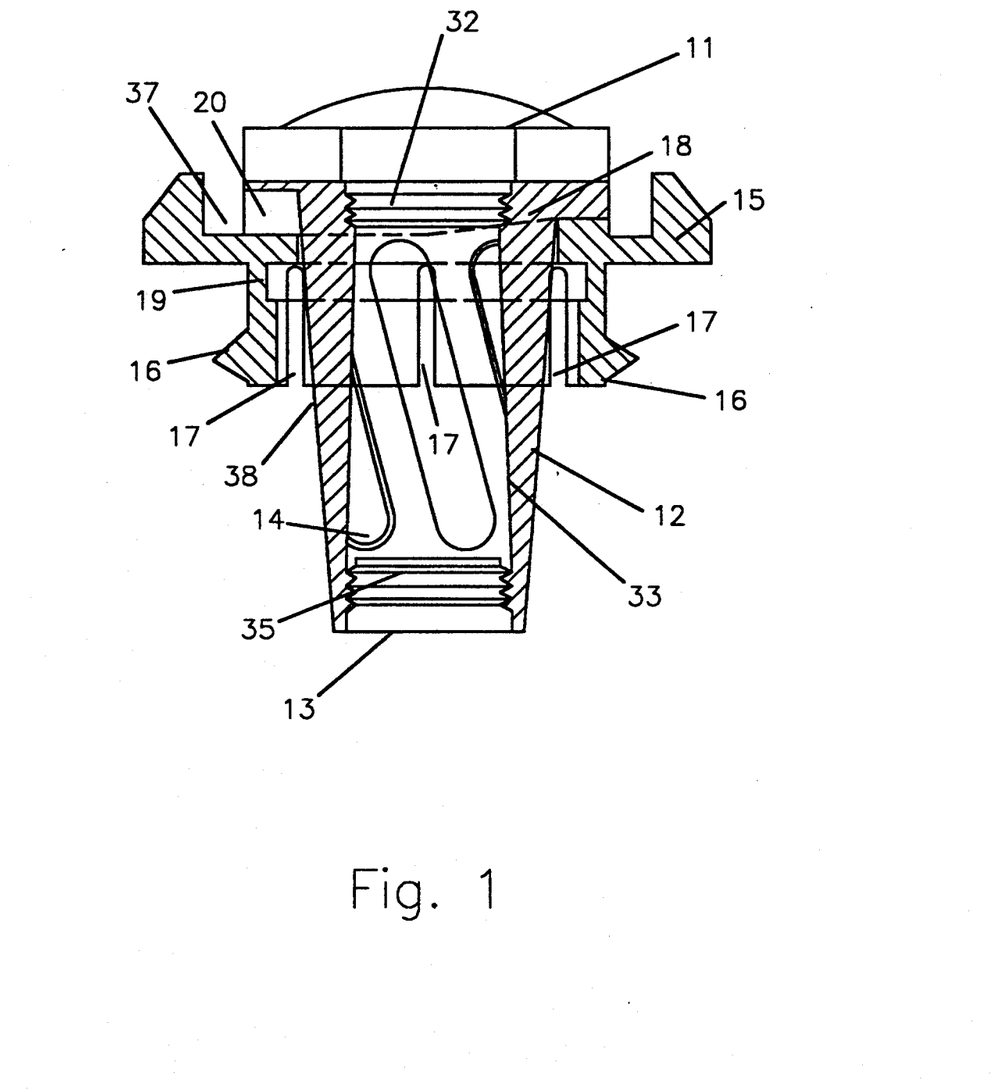
FIG. 1 is a cross-sectional plane view of the present implant showing the design and interaction of the collar and biopsy assembly.
Figure 2:
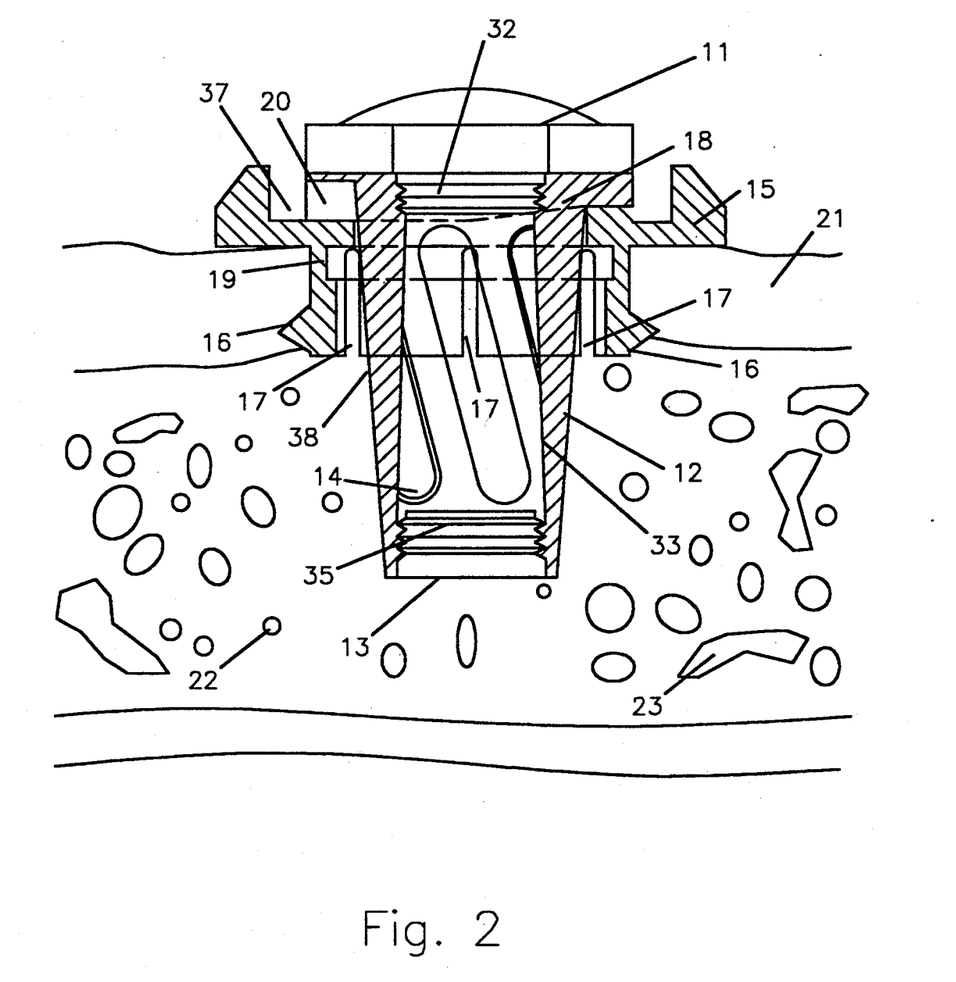
FIG. 2 is a cross-sectional plane view of the bone biopsy implant in situ in a portion of bone tissue. The assembly is rotated 90° from the orientation shown in FIG. 1 to show the ramp profile of the mating faces of the collar and cap (or tissue basket).
Figure 3:
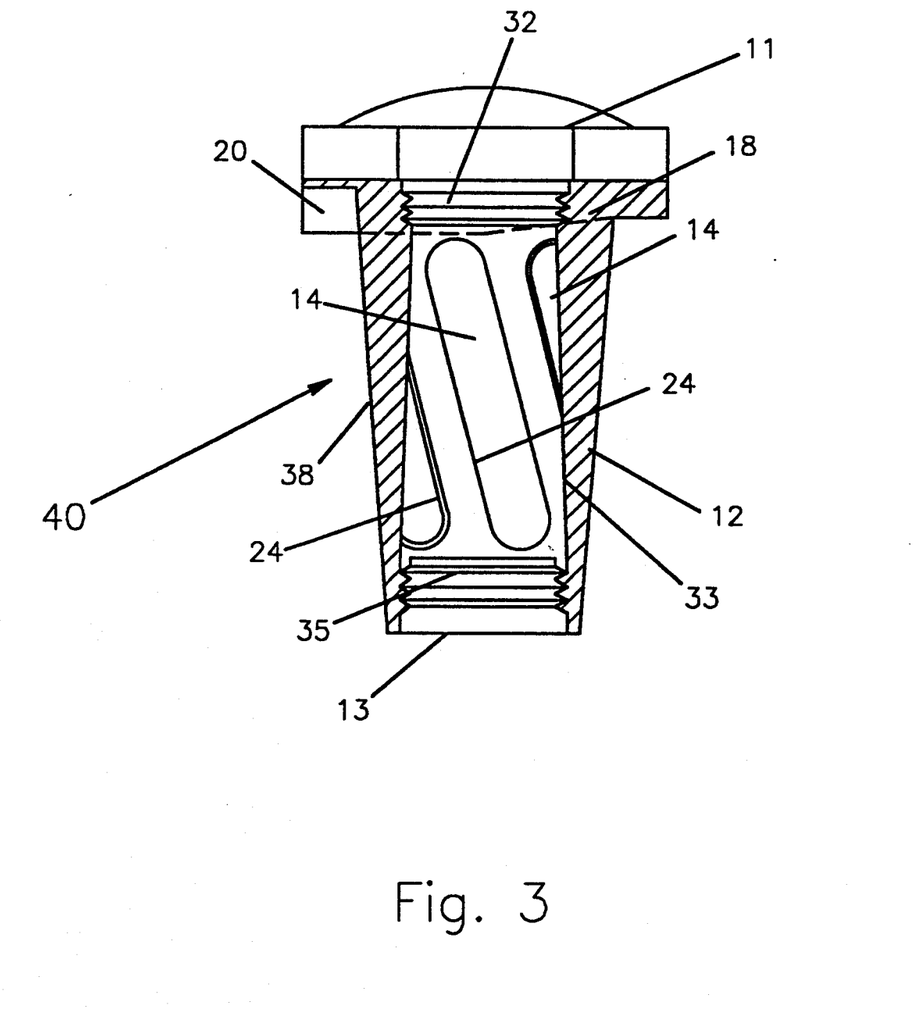
FIG. 3 is a cross-sectional plane view of the three component biopsy assembly showing the configuration of the assembly during implantation or sampling.
Figure 5A:
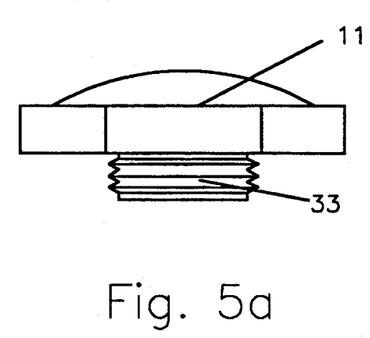
FIG. 5a is a cross-sectional plane view of the biopsy assembly cap showing its contoured shape and threaded fastener.
Figure 5B:
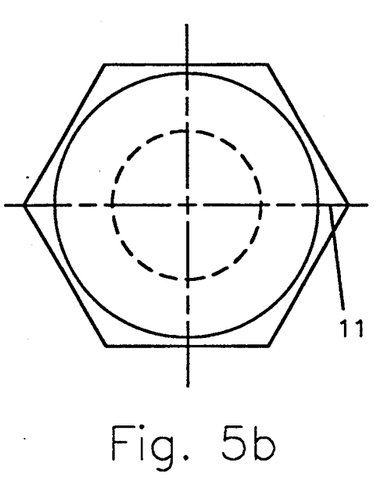
FIG. 5b is a top view of the biopsy assembly cap showing its hexagonal head.
Figure 6A:
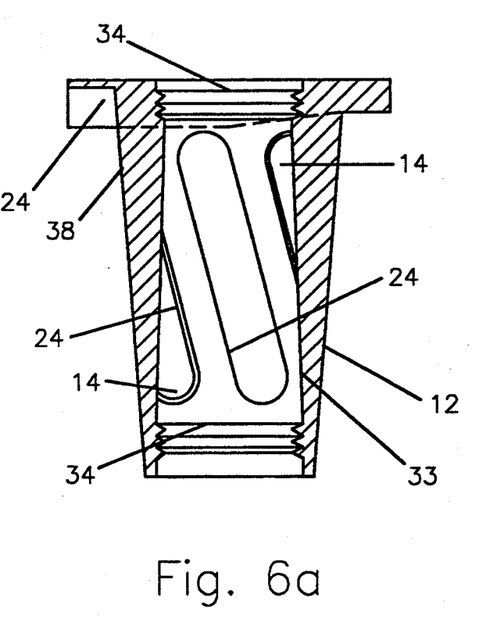
FIG. 6a is a cross-sectional view of the cutting basket showing the off longitudinal axis bone ingrowth slots with sharpened cutting edge, end cut lumen threads, and mating face ramp.
Figure 6B:
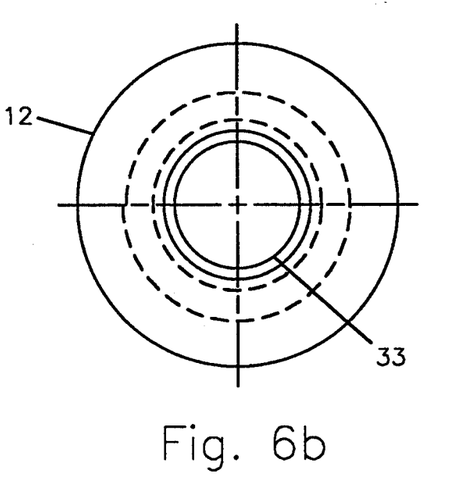
FIG. 6b is a top view of the cutting basket showing its cylindrical cross-section and lumen.
Figure 7A:
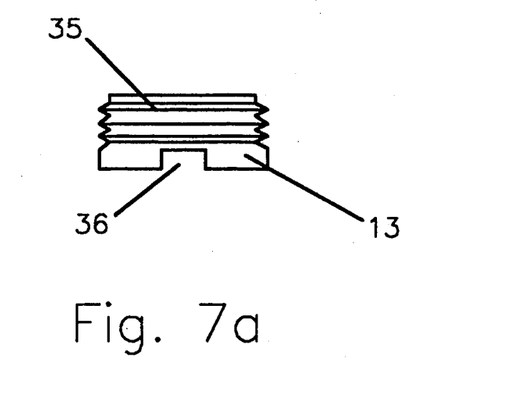
FIG. 7a is a cross-sectional view of the cutting basket end-cap showing a plurality of threads and tool slot.
Figure 7B:
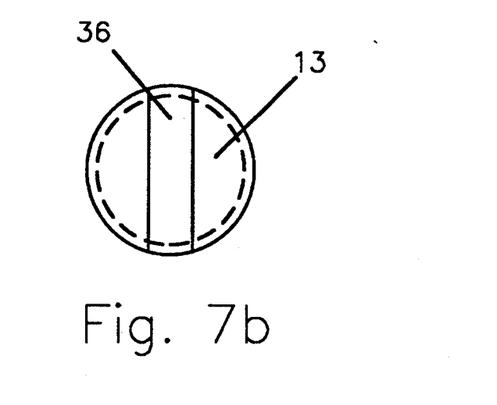
FIG. 7b is a top view of the cutting basket end-cap showing its cylindrical cross-section.
Figure 8:
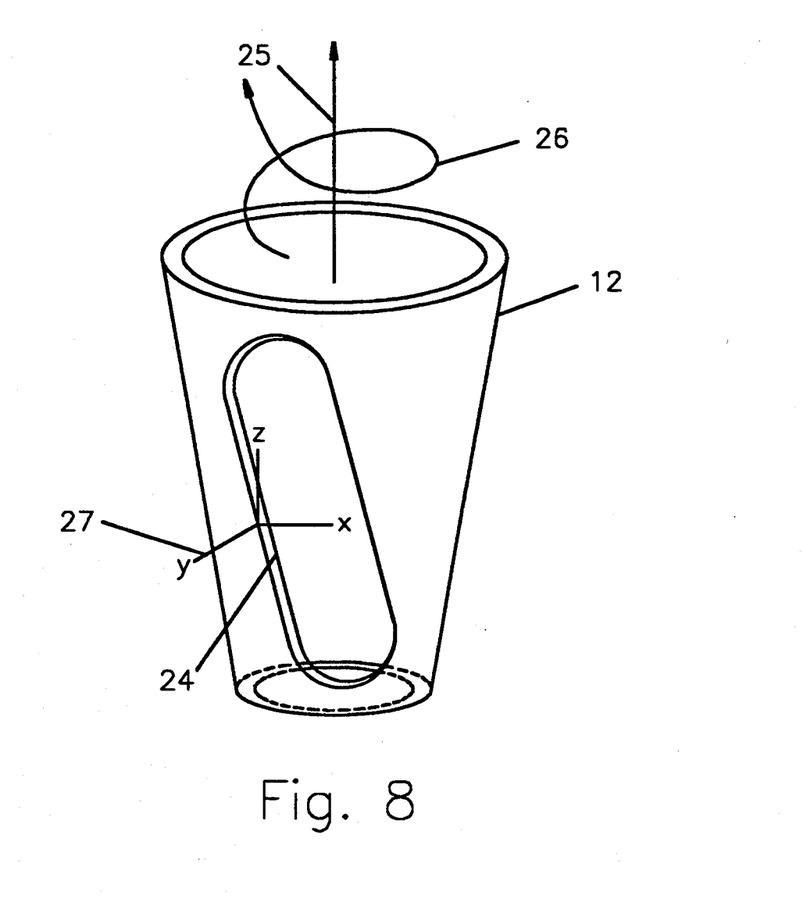
FIG. 8 is an illustration describing the three directions of bone cutting action novel to this implant design.

The preferred embodiment consists of a three component biopsy assembly (FIG. 3) and a single component collar (15) and are shown assembled in FIG. 1 and in situ in FIG. 2. As shown in FIG. 3, the biopsy assembly consists of a hexagonal cap (11) having a threaded mandrel (32) as shown in FIG. 5a, a fluted cylindrical cutting basket (12) with a tapered lumen (33) having a plurality of internal threads on both ends (34) as shown in FIG. 6a, an end-cap (13) having a plurality of threads (35) that join to the cutting basket's (12) internal plurality of threads (34) and can be rotated using the tool slot (36) shown in FIG. 7a. Additionally, the cutting basket (12) has a plurality of flutes (14) with sharpened edges (24) as shown in FIG. 8 that cut towards the direction of rotation (26) and withdrawal (25).

Figure 4A:
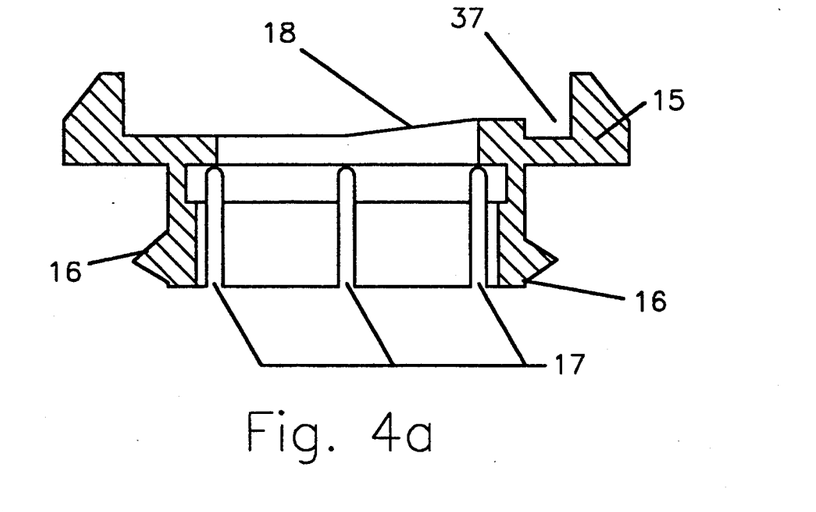
FIG. 4a is a cross-sectional view of the collar showing plurality of flutes, circumferential bead and end-face ramp.
Figure 4B:
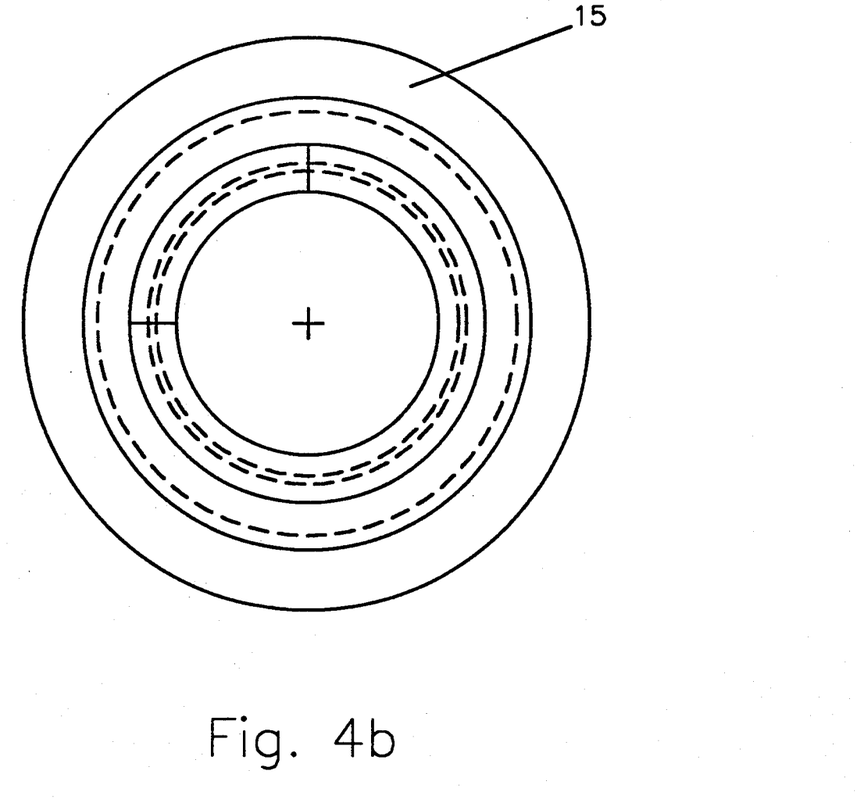
FIG. 4b is a top view of the collar showing its circular cross-section and lumen.

The collar (15) is cylindrically shaped having a circular groove (37) cut into the face of one end of the body to provide a recess for the hexagonal cap (11) and a bead (16) on the outer surface of the collar to engage the surrounding bone (as shown in FIG. 2). As shown in FIG. 4a, the collar (15) has a plurality of flutes (17) cut from the end having the bone locking bead (16) toward the ramp faced end of the collar (15) and a contoured ramp (18) and collar end-face which provides a recess for the hexagonal cap (11) to minimize overlying tissue irritation. The flutes (17) allow the cylindrical walls of the collar near the end with the bead (16) to strain towards the centrum of the collar (15) when inserting or removing from a bone defect with a size equal to the diameter of the collar (15) but less than the combined diameter of the collar (15) and bead (16). The elastic deforming action of the fluted portion of the collar (15) acts to push the bead (16) into the surrounding bone (21) and cause immediate locking of the collar (15) following insertion. The collar flutes (17) are cut with smooth edges to promote bone ingrowth and collar torsional resistance in bone when rotating the biopsy assembly to acquire tissue (12 and 13).

As illustrated in FIG. 1 and FIG. 2, the collar (15) and cutting basket (12) or in an alternate embodiment the hexagonal cap (11) each have integral mating ramps at their end-face junction. The mating surfaces (18 and 20) of the collar (15) and cutting basket (12) or alternately the hexagonal cap (11) form a concentrically oriented ramp along their opposing end-faces. These ramps (18 and 20) cause the biopsy assembly to withdraw from the lumen of the collar when the hexagonal cap (11) is rotated. Finally as shown in FIG. 1 and FIG. 2 the collar (15) is grooved within its lumen to allow the placement of an elastomeric seal ring (19). This elastomeric seal ring (19) impedes extravasation and allows the biopsy assembly to move relative to the collar (15).

One of the principal novel features of the BBI is the interaction between the collar (15) and biopsy assembly (as shown in FIG. 3) which causes the biopsy assembly to withdraw from the collar. When the biopsy assembly is rotated the cutting basket ramp (20) rides up the collar ramp (18). The direction of rotation (26) and cutting basket (12) translation (25) during biopsy acquisition are shown in FIG. 8. As illustrated by the Cartesian coordinate system (27) originating from the sharpened inner edge (24) of the cutting basket flute (14) in FIG. 8, this rotation-translation (25 and 26) withdrawal action combined with the external taper of the cutting basket (12) cause three directional components of motion at the flute's (14) sharpened inner edge (24). Furthermore, the off longitudinal axis orientation of the cutting basket flutes (14) can be varied from zero to 90 degree to impart varying degrees of cutting (defined here as sliding of the sharpened edge of the flute (14) relative to tissue (12 and 13)) or shearing (defined here as pushing of the sharpened edge of the flute (14) through tissue (12 and 13)). The greatest component of cutting motion is in the Z-direction as shown in FIG. 8. The greatest component of shearing is due to rotation (26) and is in the X-direction. The cutting basket's (12) external taper (38) can be varied over it's length from substantially zero degrees of taper to some functional taper angle less than 90 degrees to impart varying magnitudes of motion tending to pull the sharpened edge of the flute (14) away from surrounding tissue (22 and 23) when the biopsy assembly withdraws due to its rotation. The greatest component of the pulling action is along the Y-direction, as shown in FIG. 8.

DESCRIPTION OF THE ALTERNATE EMBODIMENT

Figure 9A:
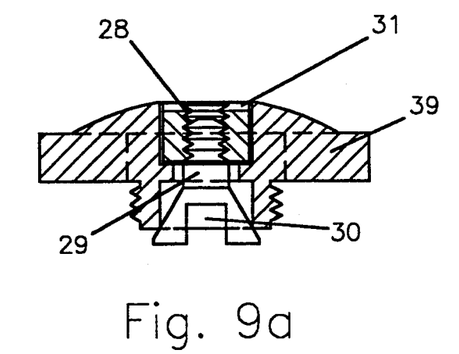
FIG. 9a is a cross-sectional view of the biopsy assembly cap with material clamp facility.
Figure 9B:
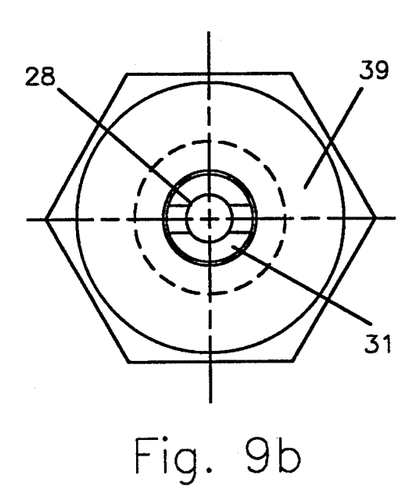
FIG. 9b is a top view of the biopsy assembly cap with material clamp facility.
Figure 10A:
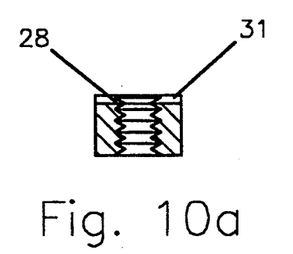
FIG. 10a is a cross-sectional view of the material fixation mandrel nut.
Figure 10B:
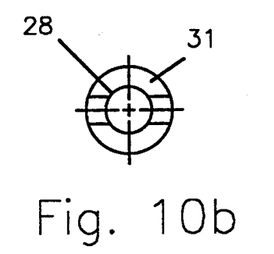
FIG. 10b is a top view of the material fixation mandrel nut.
Figure 11A:
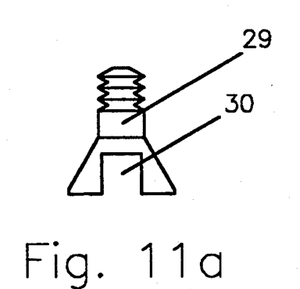
FIG. 11a is a cross-sectional view of the material fixation mandrel.
Figure 11B:
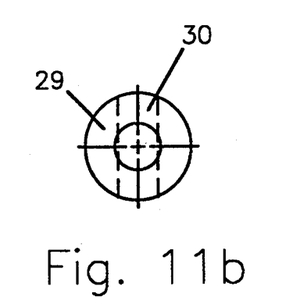
FIG. 11b is a top view of the material fixation mandrel.

A bone biopsy implant having a facility for the fixation of a biomaterial to be tested in osseous tissue (22 and 23) that allows the placement of a test material in the lumen (33) of the cutting basket (12) and the subsequent retrieval of this material with recently healed surrounding tissue (22 and 23). This alternate embodiment, shown in FIG. 9a and FIG. 9b, consists of a modified biopsy assembly hexagonal cap (39) that has a circular hole running along its central axis having varying inside diameters and a mandrel (29) and nut (28) assembly for the fastening of test materials. The mandrel (29), shown in FIG. 11a and FIG. 11b, is generally cylindrical with an increasing taper at one end, a plurality of threads on the cylindrical outer surface adjacent to the opposite end of the mandrel and a slot (30) in the end face of the mandrel having the greatest outside diameter. The nut (28), shown in FIG. 10a and FIG. 10b, is generally cylindrical with a hole through the cylinder that is oriented along the longitudinal axis having a plurality of threads on its inner surface and a slot (31) cut along the face of one end. The mandrel slot (30) provides clamping means for a test material through the interaction of the nut (28), mandrel (29) and hexagonal cap (39) so that in assembly when the nut (28) is tightened the mandrel (29) is withdrawn into the end of the hexagonal cap causing the width of the mandrel slot (30) to lessen thus pinching and fastening the test material.

OPERATION OF INVENTION

The bone biopsy implant collar (15) operates when placed in a circular hole in bone by mechanically locking to the internal surface of the hole. As the collar (15) is pushed into the hole, the bead (16) on the outer surface of the fluted end of the implant forces the walls of the fluted end to strain towards the centrum of the collar. This movement of the walls of the collar (15) is required because the outside diameter of the collar (15) in the area of the bead (16) is greater than the inside diameter of the hole. This elastic strain forces the bead (16) into the internal surface of the hole causing the implant to resist forces tending to push the collar into bone or pull the collar from the hole. In the case of a bone plate, the bead (16) may reach through the hole and expand outward causing the bead (16) to reach past the lip on the backside of the hole.

Once the collar (15) is fixed in bone, the biopsy assembly, as shown in FIG. 3, is placed in the lumen of the collar so that the cutting basket (12) reaches well into bone and the mating faces of the ramps (18 and 20) are in contact. The biopsy assembly is rotated in the collar (15) so that the biopsy assembly is fully recessed in the collar (15). Once the collar (15) and biopsy assembly are in place, overlying soft-tissue is closed and bone healing and migration into the lumen (33) of the biopsy begins.

Following healing, the bone biopsy implant is surgically exposed for removal of the biopsy assembly with bone tissue (22 and 23). Once exposed, the hexagonal cap (11) of the biopsy assembly is rotated to cut tissue at the flutes (14) of the cutting basket (12) and cause the biopsy assembly to withdraw from the collar (15) and bone.

Following removal of the biopsy assembly a new assembly can be placed in the collar (15). Alternatively, if treatment is to be concluded, the collar can be pulled from the bone because of the elastic action of the walls of the fluted end of the collar (15).

I claim:

1. A bone biopsy implant for biopsy of bone and marrow, the bone having a medullary compartment which contains the marrow therein, and endoscopic access to the medullary compartment of the bone that can be easily explanted following completion of treatment, the implant comprising:
   a collar having
      a generally cylindrical first outer surface,
      a longitudinally oriented first lumen,
      a predetermined first length terminating in two ends,
      a first plurality of longitudinally oriented flutes,
      at least one bead on the firs outer surface adjacent to one of the two ends that runs circumferentially thereto, and
      a first flange on the other of the two ends, the first flange having a first face facing away from said at least one bead and a first ramp on the first face, the first ramp being concentrically oriented relative to the first lumen;
   said first lumen having a generally smooth wall extending from one of said two ends to the other of said two ends;
   each of said first plurality of flutes penetrating the first outer surface leaving an opening into the first lumen;
   a biopsy assembly having
      a middle component having a predetermined second length terminating in a first end and a second end;
      a first end cap attached to the first end; and
      a second end cap attached to the second end;
   said middle component being a cutting basket having
      a tapered cylindrical second outer surface with means for attaching the first and second end caps, the cutting basket having a first longitudinal axis,
      a second plurality of flutes, a tapered second lumen, and a second flange adjacent to the first end, the second flange having a second ramp, wherein when the biopsy assembly and the collar are in an assembled position the cutting basket is within the first lumen and the second ramp matchingly mates with the first ramp and when the biopsy assembly is to be withdrawn from the collar the biopsy assembly is rotated within the first lumen such that the second ramp rides up the first ramp causing a translational movement of the biopsy assembly relative to the collar along the first longitudinal axis and each of said second plurality of flutes penetrating the second outer surface leaving an opening into the second lumen, having sharpened edges, and being oriented at an angle between zero and ninety degrees with respect to the first longitudinal axis of the cutting basket.

2. A bone biopsy implant as described in claim 1, wherein said first plurality of flutes extend to the end of the collar having the at least one bead such that when installing the collar in a bone defect the at least one bead causes a portion of the collar in an area where the first plurality of flutes penetrate the outer surface to strain from a first position towards the first longitudinal axis to a second position, when pushed through the bone defect and to then elastically return from the second position to the first position once the at least one bead has penetrated the bone defect into the medullary compartment.

3. A bone biopsy implant as described in claim 1, where the tapered cylindrical outer surface and the angle of orientation of the second plurality of flutes complement the rotation about the first longitudinal axis and translation along the first longitudinal axis of the biopsy assembly during withdrawal from the collar to impart three directions of movement to the sharpened edges allowing the sharpened edges to simultaneously move along the first longitudinal axis in the direction of withdrawal, perpendicularly toward the first longitudinal axis by action of the tapered cylindrical outer surface and tangentially about the first longitudinal axis during rotation of the biopsy assembly.

4. A bone biopsy implant as described in claim 1, wherein the implant is made of at least one biocompatible material.

5. A bone biopsy implant as described in claim 4, wherein the at least one biocompatible material is selected from the group consisting of titanium, stainless steel, glass, ceramics and combinations thereof.

6. A bone biopsy implant as described in claim 1, wherein when the implant is in an installed position the first and second pluralities of flutes are positioned relative to each other so as to leave an opening extending from the first outer surface into the second lumen.

7. A bone biopsy implant as described in claim 1, wherein the second length is greater than the first length such that a portion of the second plurality of flutes is exposed by extending beyond the end of the collar having the at least one bead.

8. A bone biopsy implant as described in claim 1, further comprising means for sealing between the collar and the biopsy assembly so as to stop hemorrhage between the first lumen and the second outer surface when the implant is in an installed position.

9. A bone biopsy implant as described in claim 8, where the first lumen has a circumferential groove in the generally smooth wall thereof and the means for sealing is an elastomeric seal, the elastomeric seal being located in the circumferential groove.

10. A bone biopsy implant as described in claim 1, wherein the at least one bead has a form selected from the group consisting of a sharp thread-like profile and a gentle bulging contour.

11. A bone biopsy implant as described in claim 1, further comprising means for fastening a test material to the implant within the second lumen.

12. A bone biopsy implant as described in claim 11, where the means for fastening comprises the first end cap having an inside end, an outside end, a second longitudinal axis, a first circular hole running along the second longitudinal axis from the inside end to the outside end, the first hole having a first diameter adjacent to the inside end, a mandrel and a nut; wherein said mandrel has a generally cylindrical portion with an increasing taper portion adjacent thereto, the generally cylindrical portion having a plurality of threads and the increasing taper portion has an end face with a slot therein, the slot having a first width, the end face having a second diameter greater than the first diameter; and when in an installed position the cylindrical portion having been inserted into the first circular hole via the inside end is located within the first circular hole with the increasingly taper portion located adjacent to the inside end and within the second lumen, and the nut threadedly engages the plurality of threads of the cylindrical portion, with the nut being tightenable onto the cylindrical portion by an external force, said slot providing clamping means for the test material through the intersection of the nut, the mandrel and the first end cap so that in assembly when the nut is tightened the mandrel is withdrawn into the first circular hole causing the slot to decrease from the first width to a second width which is less than the first width so as to pinch and fasten the test material thereto.

13. A bone biopsy assembly for biopsy of bone and marrow, the bone having a medullary compartment which contains the marrow therein, the assembly comprising a middle component having a predetermined length terminating in a first end and a second end;

a tint end cap attached to the first end; and a second end cap attached to the second end;

said middle component being a cutting basket having a tapered cylindrical outer surface with means for attaching the first and second end caps, the cutting basket having a longitudinal axis, a plurality of flutes, a tapered lumen, and means for explanting the biopsy assembly from a bone defect which causes a translational movement of the biopsy assembly relative to the defect in the bone along the longitudinal axis and each of said plurality of flutes penetrating the outer surface leaving an opening into the lumen, having sharpened edges, and being oriented at an angle between zero and ninety degrees with respect to the longitudinal axis of the cutting basket.

* * * * *